United States Patent
Zeng et al.

(10) Patent No.: US 10,482,680 B2
(45) Date of Patent: Nov. 19, 2019

(54) ABLATION THERAPY CONTROL BASED ON MULTI-PARAMETER GRAPHICAL MAPS

(71) Applicant: CARDIOINSIGHT TECHNOLOGIES, INC., Cleveland, OH (US)

(72) Inventors: Qingguo Zeng, Solon, OH (US); Charulatha Ramanathan, Solon, OH (US); Venkatesh Vasudevan, Beachwood, OH (US); Remi Dubois, Paris (FR); Ping Jia, Solon, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 614 days.

(21) Appl. No.: 14/158,320

(22) Filed: Jan. 17, 2014

(65) Prior Publication Data
US 2014/0200874 A1 Jul. 17, 2014

Related U.S. Application Data

(60) Provisional application No. 61/753,764, filed on Jan. 17, 2013.

(51) Int. Cl.
| | |
|---|---|
| *G06T 19/20* | (2011.01) |
| *A61B 5/00* | (2006.01) |
| *A61B 5/0432* | (2006.01) |
| *A61B 5/0476* | (2006.01) |
| *G09B 23/30* | (2006.01) |
| *G06T 11/00* | (2006.01) |
| *A61B 18/14* | (2006.01) |
| *A61N 1/362* | (2006.01) |
| *A61N 7/02* | (2006.01) |
| *A61B 17/00* | (2006.01) |
| *A61B 18/00* | (2006.01) |
| *A61B 18/02* | (2006.01) |
| *A61B 90/00* | (2016.01) |

(52) U.S. Cl.
CPC ............ *G06T 19/20* (2013.01); *A61B 5/0432* (2013.01); *A61B 5/0476* (2013.01); *A61B 5/743* (2013.01); *G06T 11/001* (2013.01); *G09B 23/30* (2013.01); *A61B 5/7221* (2013.01); *A61B 18/1492* (2013.01); *A61B 2017/00053* (2013.01); *A61B 2018/0072* (2013.01); *A61B 2018/00351* (2013.01); *A61B 2018/00642* (2013.01); *A61B 2018/00726* (2013.01); *A61B 2018/00732* (2013.01); *A61B 2018/00767* (2013.01); *A61B 2018/00839* (2013.01); *A61B 2018/0212* (2013.01); *A61B 2090/376* (2016.02); *A61B 2562/046* (2013.01); *A61N 1/362* (2013.01); *A61N 7/02* (2013.01); *G06T 2210/41* (2013.01); *G06T 2219/2012* (2013.01)

(58) Field of Classification Search
None
See application file for complete search history.

(56) References Cited

U.S. PATENT DOCUMENTS

| | | |
|---|---|---|
| 2003/0013957 A1 | 1/2003 | Bjaerum et al. |
| 2007/0073179 A1 | 3/2007 | Afonso et al. |
| 2009/0053102 A2* | 2/2009 | Rudy ............... A61B 5/0402 422/24 |
| 2011/0060221 A1 | 3/2011 | Fan et al. |
| 2011/0144510 A1 | 6/2011 | Ryu et al. |
| 2012/0029504 A1 | 2/2012 | Afonso et al. |
| 2012/0101398 A1 | 4/2012 | Ramanathan et al. |

FOREIGN PATENT DOCUMENTS

| | | |
|---|---|---|
| CN | 101443792 A | 5/2009 |
| WO | 2007/146864 A2 | 12/2007 |

OTHER PUBLICATIONS

Walter, "Visualization of image data from cells to organisms," Nature methods, vol. 7, p. S26-S41, 2010.*
Silverstein, et al., "Automatic Perceptual Color Map Generation for Realistic Volume Visualization", J Biomed Inform. 2008, retrieved on [May 18, 2014]. Retrieved from Internet: URL:http://ww.ncbi.nlm.nih.gov/pmc/articles/PMC2651027/pdf/nihnms81357.pdf> entire document.
International Application No. PCT/US2014/012077, International Search Report and Written Opinion; Date of Completion: May 18, 2014; dated May 27, 2014; 10PP.
European Search Report for Application No. EP 14740379, dated Aug. 25, 2016.
Kuanquan Wang, et al., "Effective transfer function for interactive visualization and multivariate volume data", Biomedical Engineering and Informatics (BMEI), 2011 4th International Conference on, IEEE. Oct. 15, 2011, pp. 272-276, XP032071473.
Chinese Office Action—Chinese Application No. 201480010879.6; Applicant: Cardioinsight Technologies, Inc.; Title: Multi-Parameter Physiological Mapping; Filed Jan. 17, 2014, Office Action dated Feb. 24, 2017, 25 pgs.
Jonathan C. Silversein, et al.; Journal of Biomedical Informatics; "Automatic Perceptual Color Map Generation for Realistic Volume Visualization"; Published Dec. 2008; (Available online Mar. 13, 2008); pp. 927-935.

(Continued)

*Primary Examiner* — G Steven Vanni
(74) *Attorney, Agent, or Firm* — Tarolli, Sundheim, Covell & Tummino LLP

(57) ABSTRACT

A map generator can be programmed to generate a multi-parameter graphical map by encoding at least two different physiological parameters for a geometric surface, corresponding to tissue of a patient, using different color components of a multi-dimensional color model such that each of the different physiological parameters is encoded by at least one of the different color components.

7 Claims, 6 Drawing Sheets

(56) References Cited

OTHER PUBLICATIONS

Chinese Office Action—Chinese Application No. 201480010879.6; Applicant: CardioInsight Technologies, Inc.; Titlte: Multi-Parameter Physiological Mapping; Filed Jan. 17, 2014, Office Action dated Oct. 24, 2017.

* cited by examiner

ABLATION THERAPY CONTROL BASED ON MULTI-PARAMETER GRAPHICAL MAPS

RELATED APPLICATION

This application claims the benefit of U.S. Provisional Patent Application No. 61/753,764 filed Jan. 17, 2013 and entitled MULTI-PARAMETER PHYSIOLOGICAL MAPPING, the entire contents of which is incorporated herein by reference.

TECHNICAL FIELD

This disclosure relates to mapping multiple physiological parameters.

BACKGROUND

Electrophysiology is the study of the electrical properties of biological cells and tissues. Electrophysiology is utilized to measure electrical activity of biological tissue of patients in a variety of applications, including electroencephalography, electrocardiography, electromyography, electrooculography and the like. Detecting and visualizing information derived from the sensed electrical signals can be relevant to clinical studies as well as diagnosing patient conditions.

SUMMARY

This disclosure relates to mapping multiple physiological parameters.

As one example, one or more non-transitory computer-readable media includes instructions executable by a processor. The instructions can include a map generator programmed to generate a multi-parameter graphical map by encoding at least two different physiological parameters for a geometric surface, corresponding to tissue of a patient, using different color components of a multi-dimensional color model such that each of the different physiological parameters is encoded by at least one of the different color components.

In another example, a method can include storing physiological parameter data in memory. The physiological parameter data can represent at least two different physiological parameters for tissue of a patient. Each of the at least two different physiological parameters can be encoded using different color components of a multi-dimensional color model, such that each of the different physiological parameters is encoded by at least one of the different color components. A multi-parameter graphical map can be generated for a geometric surface, corresponding to the tissue of the patient, based on the encoding such that the different physiological parameters are visualized in the multi-parameter graphical map.

DETAILED DESCRIPTION

This disclosure relates to generating a map of multiple parameters of electrophysiological information concurrently (e.g., in a single electroanatomic map). For example, a plurality of related parameters can be mapped to a common geometric surface, and be encoded according to a multi-component color model. For the example of electrocardiographic mapping, one of two related cardiac parameters can be mapped to one or more components of the color model and the other of the related parameters can be mapped to another component of the color model. The resulting map can be visualized in an output display. Thus, by knowing which of the multiple cardiac parameters is encoded by which component(s) of the color model (e.g., via providing a scale that identifies the encoding), a user can glean more information from the resulting output map than traditional mapping that encodes a signal parameter in a given color model.

As used herein, the term "color model" can refer to an abstract mathematical model (e.g., implemented as machine readable instructions) describing the way colors can be represented as tuples of numbers, typically as three or four color components. Examples of color models that can be used by systems and methods disclosed herein include HSV (hue, saturation, value), HSL (hue, saturation, lightness/luminance), HIS (hue, saturation, intensity), RGB (red, green, blue), CMYK (cyan, magenta, yellow, key), YIQ or the like. Other color encoding schemes can be utilized.

While many examples herein are described in the context of cardiac electrical signals, it is to be understood that the approaches disclosed herein are equally applicable to other electrophysiological signals, such as electroencephalography, electromyography, electrooculography and the like from which an electroanatomic graphical map can be generated.

Figure 1:
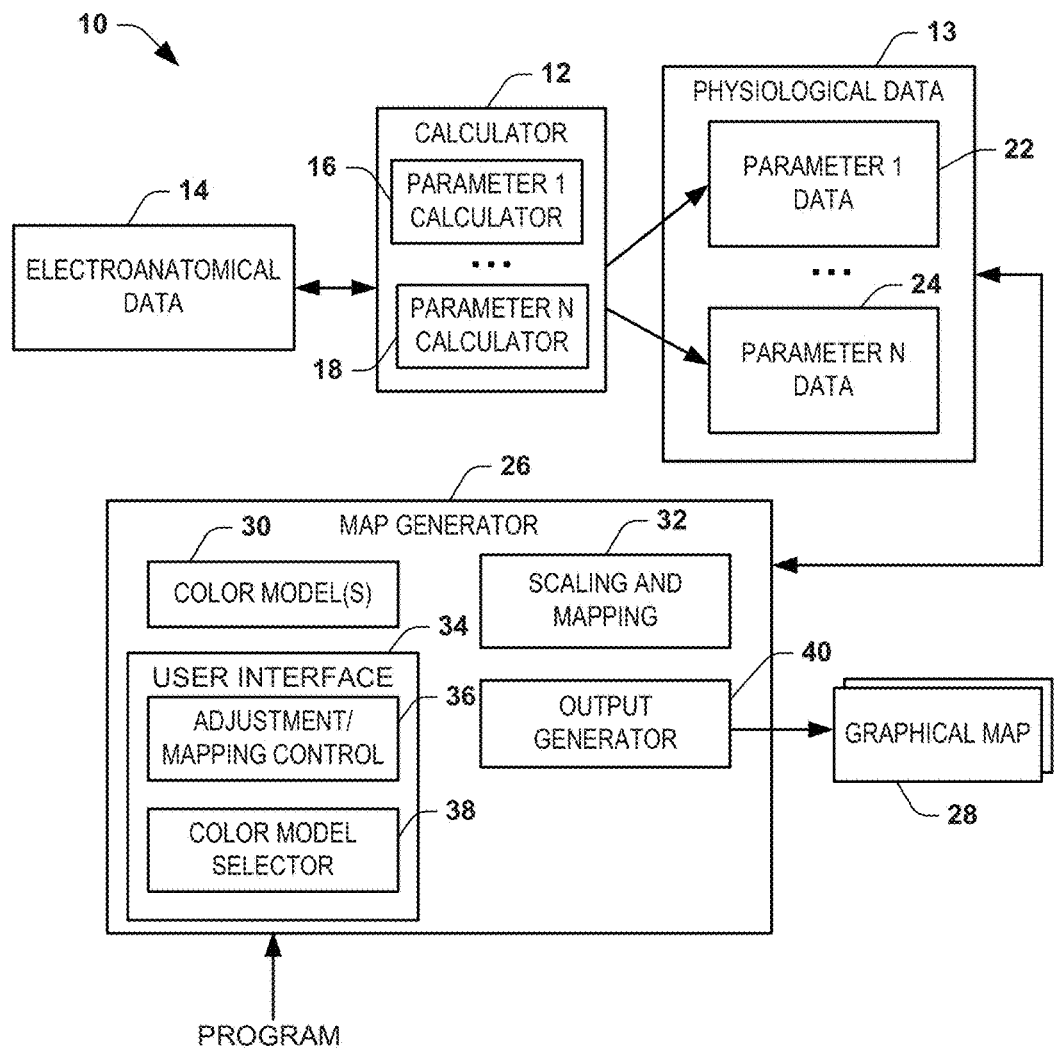
FIG. 1 depicts an example of a system for mapping multiple physiological parameters.

FIG. 1 depicts an example of a system 10 can be implemented to perform multi-parameter physiological mapping. The system 10 includes a calculator 12 programmed to compute (e.g., quantify) physiological data 13 that includes data representing two or more parameters based on electroanatomical data 14. The electroanatomical data 14 can include a combination of electrical data and geometry data for the patient that describes electrical activity at a plurality of anatomical locations over one or more time intervals. The electroanatomical data 14 can be stored in memory (e.g., one or more non-transitory computer readable media). In some examples, the electroanatomical data 14 can be provided as electrograms or other electrical waveforms representing electrical activity for corresponding anatomical locations over one or more time intervals.

In some examples, the anatomical locations for which the electrical data corresponds can be represented as nodes distributed over a geometric surface, which can be a two-dimensional or three-dimensional surface. For example, the geometric surface can be a surface of an anatomical structure, such as tissue of a patient (e.g., human or other animal), or it can be an arbitrary surface for spatially depicting electrical information. In some examples, the patient tissue can be cardiac tissue, such that the geometric surface corresponds to an epicardial surface, an endocardial surface or another cardiac envelope. The geometric surface can be patient specific (e.g., based on imaging data for the patient), it can be a generic model of the surface or it can be a hybrid version of a model that is customized based on patient-specific data (e.g., imaging data, patient measurements and/or the like). The electroanatomical data 14 thus can characterize electrical potentials as well as the location of such nodes distributed across any such geometric surface (e.g., patient tissue).

As a further example, the electrical component of the electroanatomical data 14 can correspond to electrophysiological signals, such as can correspond to electrophysiological signals obtained by one or more electrodes or otherwise derived from signals obtained by such electrodes. For instance, the electrodes can be applied to measure the electrical activity non-invasively, such as may be positioned over a patient's body surface, such as the patient's head (e.g., for electroencephalography), a patient's thorax (e.g., for electrocardiography) or other noninvasive locations. The electroanatomical data 14 thus can correspond to body surface measured electrical signals. In other examples, as disclosed herein, the electroanatomical data 14 can include electrical signals reconstructed onto another surface based on the direct body surface measurements. As another example, the electrical portion of the electroanatomical data 14 can be measured invasively, such as by one or more electrodes positioned within a patient's body (e.g., on a lead or a basket catheter during an EP study or similar procedure). In yet other examples, the electroanatomical data 14 can include or be derived from a hybrid approach that includes both non-invasively measured electrical signals and invasively measured electrical signals associated with a geometric surface corresponding to patient tissue.

By way of further example, a region of the heart can be represented as the geometric surface, which can be a two-dimensional surface or a three-dimensional surface (e.g., an epicardial surface, an endocardial surface or other cardiac envelope). The geometric surface thus can represent a portion up to the entire surface of the heart. The geometric surface further can be patient specific (e.g., based on imaging data for the patient) or it can be a generic model or it can be a model that is generated based on patient-specific data (e.g., imaging data, patient measurements and/or the like). The geometric surface can include a plurality of discrete locations, also referred to herein as nodes.

In the example of FIG. 1, the calculator 12 can include two or more parameter calculators 16 and 18, demonstrated as PARAMETER CALCULATOR 1 through PARAMETER CALCULATOR N, where N is a positive integer denoting the number of calculators (N>1). Each parameter calculator 16 and 18 is programmed to compute physiological parameter data 22 and 24 for each point of a geometric surface of interest. The computed parameter data 22 and 24 can be related spatially over a geometric surface (e.g., an endocardial surface, an epicardial surface or other cardiac envelope). Additionally or alternatively, the computed parameter 22 and 24 can be related temporally and spatially. For instance, the computed parameter values can correspond to the same spatial locations across the geometric surface as well as for the same time or time interval, such as can be tracked by time indices associated with the electrical data 14, based on which the calculators 16 and 18 compute the parameter data. That is, the different parameter data 22 and 24, while representing different physiological information, can be temporally and spatially consistent. Additionally, each of the calculators 16 and 18 can compute the physiological data 13 for one or more time periods, which can be specified based on a user input. In this way, the physiological data 13 can be temporally consistent for each parameter via time indices associated with the data.

As one example, one of the calculators 16 can be programmed to compute a phase for each of the plurality of nodes across a geometric surface for a given time interval based on the electroanatomical data 14. One or more other of the calculators 18 can be programmed to compute other cardiac information for the geometric surface based on the same the electroanatomical data 14. The resulting phase data and other computed cardiac information can be stored in the physiological data 13 as parameter data 22 and 24, respectively. Examples of the types of other cardiac information that the parameter calculator 18 can compute are disclosed with respect to FIG. 4 herein.

The computed physiological data 13 (e.g., stored as parameter 1 data 22 and parameter N data 24 in the example of FIG. 1) can be stored in memory as a table or other data structure associated with nodes distributed across the geometric surface for which the data represents. In some examples, the parameter data 22 and 24 can correspond to static data computed for a single interval. In other examples, the phase data and magnitude data can be computed for a plurality of separate intervals. The intervals may be contiguous or non-contiguous intervals.

A map generator 26 can be programmed to generate the multi-parameter graphical map 28. For example the map generator 26 can be programmed to combine different parameter data 22 and 24 representing different physiological parameters into a common graphical map 28 by encoding the different parameters based on a multi-dimensional color model 30. The color model 30 can include a plurality of color components to which different sets of the parameter data 22 or 24 can be encoded. The map generator 26 can generate a corresponding multi-parameter graphical map for a geometric surface (e.g., corresponding to patient tissue) based on the encoding of the parameter data 22 and 24 to different color components. The map generator 26 can include an output generator 40 programmed to provide an output visualization of the graphical map 28 to a display device based on mapping the different parameter data 22 and 24 to the color model 30. As a result, the different physiological parameters can be visualized concurrently in the same the multi-parameter graphical map 28.

In the example of FIG. 1, the map generator 26 can include normalizing and mapping function 32 that scales each of the parameter data 22 24 to a respective normalized scale according to the color component of the color model 30 being used to encode each parameter. The normalizing and mapping component 32, for example, can map the parameter 1 data 22 to one color component of the color model 30 and another parameter data 24 to another component of the color model.

For an example where parameter 1 data represents computed phase data and the parameter N data 24 represents magnitude, the scaling and mapping component 32 can normalize the magnitude data by mapping its range of magnitude values across a predetermined linear scale (e.g., its largest magnitude value to 1.0 and its smallest value to 0.0), which can be mapped to the range of values in the selected color component for the magnitude. For the example of HSV color model, three color components can be defined as a 1×3 vector of (h,s,v) to encode computed physiological data 13 via color scale at a given point in space and time. Continuing with the example of mapping phase and magnitude data, hue (h) can be utilized for encoding phase data 22. If saturation (s) is selected for encoding the magnitude data 24, then the second color component of saturation will encode the normalized magnitude while a third component, the value (v) component, of the HSV color model 30 can be set to a constant value (e.g., v=1 or other value) or a variable value. Similar normalization and scaling of can be utilized for mapping physiological parameters associated with a given geometric surface over a common time interval to one or more other color models.

As mentioned, the map generator 26 can include a user interface (e.g., a graphical user interface) to expose user-programmable functions. For example, the map generator 26 can include an adjustment/mapping control 36 programmed to adjust the normalizing and mapping of the map data 20 to the color model. The adjustment/mapping control 36 can adjust the normalizing and scaling that is performed (e.g., apply linear or non-linear scaling) on the parameter data 22 or 24 in response to a user input. Additionally, the adjustment/mapping control 36 can specify and control to which color component of the color model 30 each parameter is mapped. Additionally or alternatively, if a color component of the color model 30 remains unmapped, the adjustment component of the user interface can be used to specify a value for such color component. The amount of adjustments can be selectively controlled in response to a user input.

Figure 2:
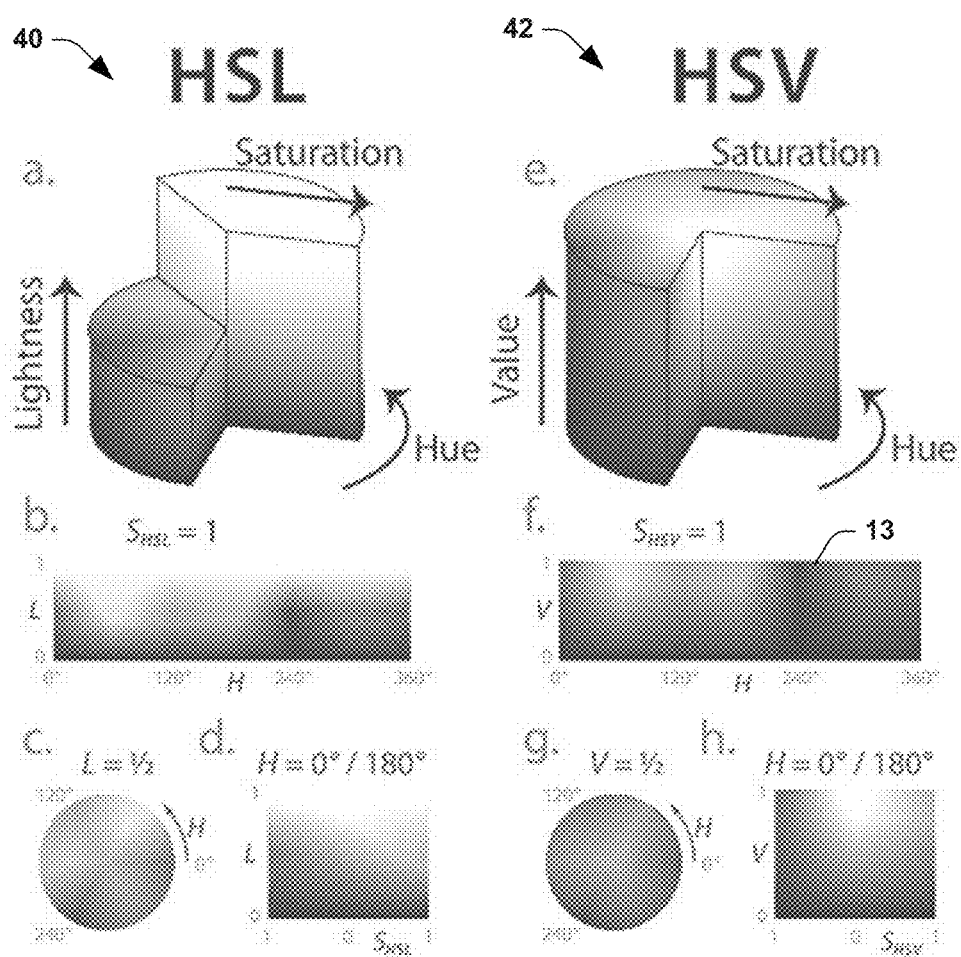
FIG. 2 depicts examples of two types of color models that can be utilized for mapping physiological information.

FIG. 2 demonstrates examples of two different color models 40 and 42 that can be utilized for encoding different physiological data parameters in a signal graphical map of a geometric surface. In the example of FIG. 2, the color model 40 is an HSL (hue, saturation, lightness/luminance) color model and the model 42 is an HSV (hue, saturation, value) color model. With reference between FIGS. 1 and 2, for the example of using the model 40, the scaling and mapping 32 can scale and map the first parameter data 22 to be encoded by one of hue, saturation or lightness and map the other parameter 24 to another of hue, saturation and lightness components that remains unmapped. Similarly, for the example of using the model 42, the scaling and mapping 32 can scale and map the first parameter data 22 to be encoded by one of hue, saturation, value and map the other parameter 24 to another of hue, saturation, value components that remains unmapped.

By way of further example, where the color model 30 is implemented as an HSV color model (e.g., see FIG. 2), the first parameter data 22 can be mapped to hue and a second set parameter data 24 can be mapped to saturation. As another example, the second parameter data 24 can be mapped to hue and the first parameter data can be mapped to value. The remaining unencoded color component can be set to a fixed value, such as unity, or a variable value. In other examples, the unencoded color component can be set to desired value, such as can be specified in response to a user input via the adjustment control 36.

The user interface 34 can also include a color model selector 38 programmed to select a which color model from a plurality of color models 30 is utilized by the map generator in response to a user input. For example, a user can selectively define not only the mapping and how the computed parameter data 22 and 24 is encoded by the color model 30 via the user interface 34, but can also employ the color model selector 38 to select which color model is utilized. For instance, the color model 30 can include a plurality of different multi-parameter color models, each of which can include two or more color components that can be selectively utilized for encoding different parameters of the physiological data 13.

In some examples, the adjustment/mapping control 36 can be programmed to map a single one of the computed parameters (e.g., phase data 22 or magnitude data 24) to a selected color component of the color model while other color components are set to fixed or predetermined variable values, such as can be utilized by the output generator 40 to generate a map that encodes a single parameter. A single parameter map can be visualized concurrently with a multi-parameter map to further allow a user to compare the respective maps and the relationship between the parameters which have been computed (e.g., in a side-by-side comparison).

In addition to normalizing the data to a predetermined scale (e.g., ranging from 0 to 1), instead of fixing the unmapped color component to a fixed value, the unmapped component can be mapped to a user defined value such as in response to a user input. For example, the unmapped component can be mapped to a variable value, such as may vary spatially and/or temporally. As another example, a user can remap color components such as hue having an angular value that is repeated by adding a predetermined angle to rotate the color hue circle (e.g., by 180 degrees). In this way different phase data can be mapped to different hues or other color components.

The scaling and mapping component 32 can also be configured to apply a linear or nonlinear mapping on the normalization and scaling that is performed. For example, gamma index correction can be implemented relative to the one of the parameters being encoded (e.g., phase data or magnitude data). Additionally or alternatively, the scaling and mapping component 32 can apply a piecewise linear scaling to approximate a desired nonlinear function.

Figure 3:
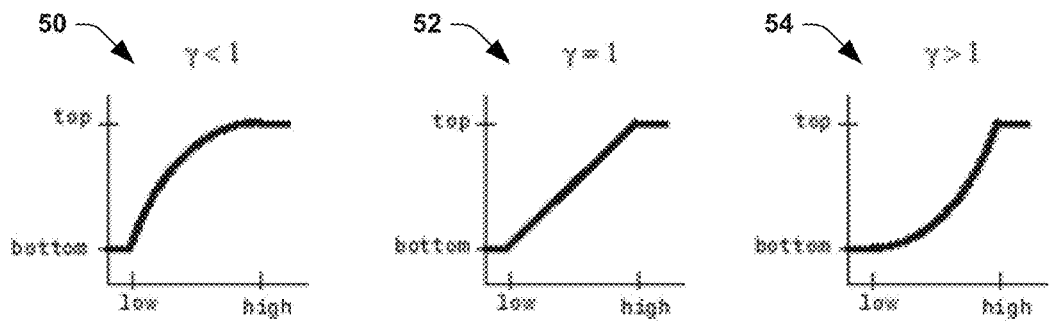
FIG. 3 is a graph of example adjustment functions that may be applied to data being encoded by a component of a color model.

The scaling and mapping function 32 can be configured to implement other adjustments and corrections for parameters being encoded by a given color model. FIG. 3 demonstrates different forms of gamma correction that can be implemented. For gamma less than 1, contrast can be enhanced as demonstrated in the left-most plot 50 in FIG. 3. The middle plot 52 of FIG. 3 demonstrates that for gamma equal 1, the output can be truncated at high and low thresholds. The right-most plot 54 in FIG. 3 demonstrates for gamma greater than 1, in which the contrast can be reduced. Those skilled in the art will understand and appreciate other forms of linear and nonlinear operations that can be applied by the scaling and mapping component 32 relative to one or more of the multi-parameter data that are being encoded by a color model for mapping on a geometric surface.

Figure 4:
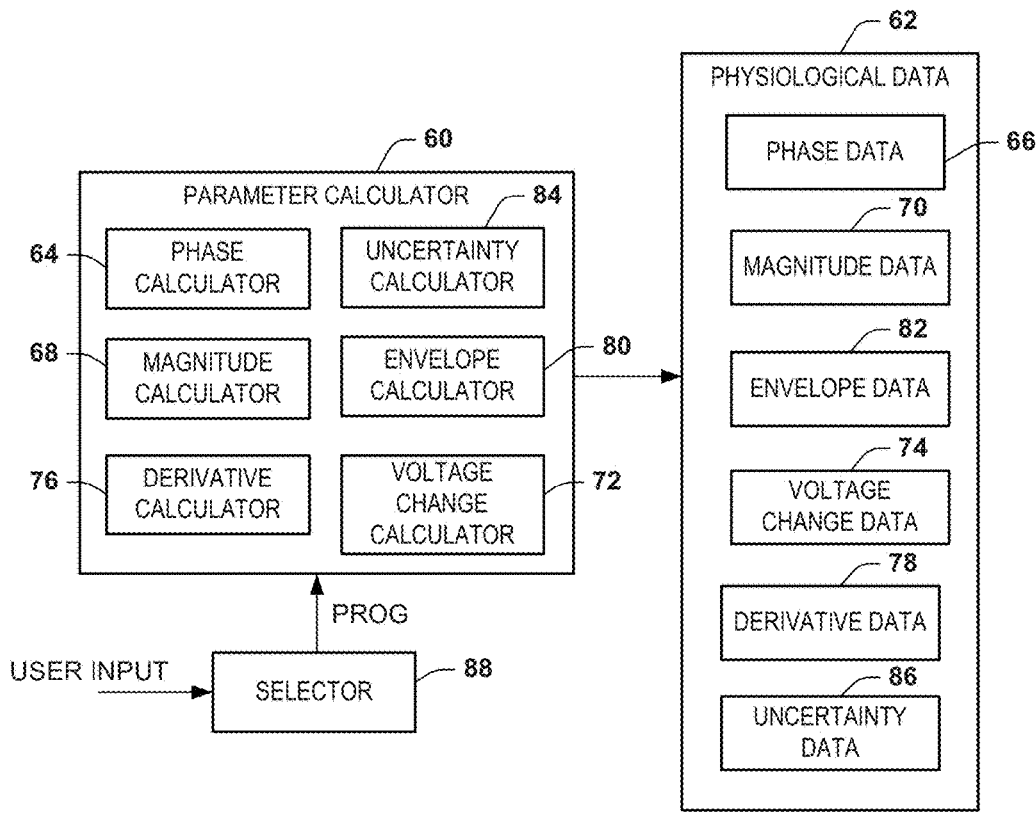
FIG. 4 depicts an example of a calculator that can be implemented in the system of FIG. 1.

FIG. 4 depicts an example of another calculator 60 that can be utilized to compute two or more parameters based on electroanatomic data (e.g., data 14 of FIG. 1). The calculator 60 can correspond to the calculator 18 in FIG. 1 as to compute physiological data 62 (e.g., corresponding to PARAMETER 1 data 22 through PARAMETER N data 24 of FIG. 1). Accordingly, reference can be made to FIG. 1 and its description for additional context for the calculator 60 and the physiological data 62. The calculator 60 and its components can be implemented as machine readable instructions that can be stored in one or more non-transitory media and be executed by a processing resource (e.g., one or more processor cores). Similarly, the data 62 can be stored in one or more non-transitory computer-readable media (e.g., one or more memory devices).

In the example of FIG. 4, the calculator 60 can include a phase calculator 64 programmed to compute phase of electrical activity for nodes distributed across a geometric surface, corresponding to patient tissue, based on the data representing the electrical activity for the geometric surface over time. Various methods can be utilized as the phase calculator. As one example, the phase calculator 64 can employ a Hilbert transform, such as the type disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized in other embodiments to determine phase. The phase calculator 64 thus can compute the phase for each of the nodes on a geometric surface for a period of time, which can be stored as phase data 66.

As a further example, the phase calculator 64 can be programmed to compute the phase by converting each cycle of electrical signal into a periodic signal as a function of time. For example, let $-\pi$ be an arbitrary beginning of the cycle; then $\pi$ is the beginning of the next cycle. The phase calculator 64 can assign each point in time in between the beginning and end of each cycle a phase value between $[-\pi, \pi]$ in an increasing manner. For instance, assume that the obtained phase is the phase of a complex number of magnitude 1; that way, each respective cycle can be converted into one circle with center at 0,0 in the complex space.

The calculator 60 can also include a magnitude calculator 68 programmed to determine an indication of magnitude of voltage potentials for the geometric surface, which can be stored as magnitude data 70. The magnitude calculator 68 can determine the magnitude of the potential for each node across the same geometric surface based on the measured and/or derived electrical signals (e.g., electrical data 14) for each respective such node.

The calculator 60 also can include a voltage change calculator 72 programmed to compute a voltage change in a moving window. The computed voltage change for each node distributed across the same geometric surface can be stored as voltage change data 74. By way of example, for each time frame, which can be defined by corresponding time indices associated with the input electrical signals for the geometric surface, the voltage change calculator 72 can compute voltage change using a window centered at the chosen time by $$\max(p_t) - \min(p_t)$$

where $p_t$ is an array of potentials centered at time t of certain length n (e.g., n=250 ms)

If the moving window is the full interval, then voltage change is a scalar.

The calculator 60 also can include a derivative calculator 76 programmed to compute a derivative of one or more signals provided by or derived from the electrical activity signals represented by the electroanatomical data 14. The derivative calculator 76 can be applied to compute a derivative of any waveform, including those stored in the physiological data or the input electrical data (e.g., corresponding to electroanatomical data 14). The derivative for each node distributed across the same geometric surface can be stored as derivative data 78. Derivatives of signals can detect quick changes better. For example, smallest value of dv/dt can be used to detect activation for potentials in a given window. The derivative data (e.g., dv/dt) can be integrated with phase data over a plurality of time intervals via encoding the phase data and the derivative data to different color components of a given color scale of a corresponding multi-parameter graphical map. Moreover, such multi-parameter graphical map can be computed over one or more time interval comprising a plurality of consecutive time indices to provide an animated dynamic map (e.g., a movie-like map) that can help to confirm activation using potentials.

As a further example, the calculator 60 can include an envelope calculator 80. The envelope calculator 80 can be programmed to compute an envelope of potentials or filtered potentials from the input electrical signals (e.g., electrical data 14). The computed envelope of potentials can be stored as envelope data 82 for each node across the geometric surface of interest. For example, the envelope calculator 80 can be programmed to perform squaring and low pass Filtering and/or a Hilbert Transform, to detect the envelope of voltage magnitude. As an example, with reference back to FIG. 1, the map generator 26 can combine the computed envelope data 82 with phase information (phase data 66) by encoding each to a different color component of a selected color model to visualize the dynamics of signal magnitude with phase across the geometric surface.

As yet another example, the calculator 18 can include an uncertainty calculator 84 programmed to compute an uncertainty metric associated with one or more other of the computed parameters stored in the physiological data 62. The computed uncertainty can be stored as uncertainty data 86. The uncertainty metric can be applied to determine an indication of a confidence for another set of data computed by the calculator 60. For example, uncertainty can be calculated for each location across the geometric surface, by evaluating similarity of signals in a small spatial neighborhood around each respective location. For instance, the uncertainty calculator can be programmed to compute an average of cross correlation for the signals in each neighborhood of a given node and compare (e.g., calculate a difference between) the computed cross correlation with the signal the signal for the given node. As a further example, in the HSV color model, the computed uncertainty data 86 can be encoded to hue or value in HSV space and the other parameter data can be encoded to a different color component, such as saturation, value or hue.

In view of the foregoing, it is to be understood that various parameters that can be calculated and utilized for generating a multi-parameter graphical map according in which different parameters are encoded by different color components of a given color scale. In order to control which parameters are utilized, a selector 88 can be employed to program the calculator 60. For example, the selector can program the calculator 60 to utilize two or more of the calculators 60 and process the input data accordingly, in response to a user input. The resulting computed physiological data 62 can be utilized by the map generator as disclosed herein. For example, the selector 88 can be exposed to a user via a graphical user interface (e.g., the user interface 34 of FIG. 1). Since the electrical signals that the calculator 60 processes can be measured concurrently across a geometric region (e.g., over up to the entire heart surface), the computed physiological data 62 likewise can be spatially and temporally consistent across the geometric region of interest. A user can selectively generate maps based on the computed parameters to visualize relationships among different parameter.

Figure 5:
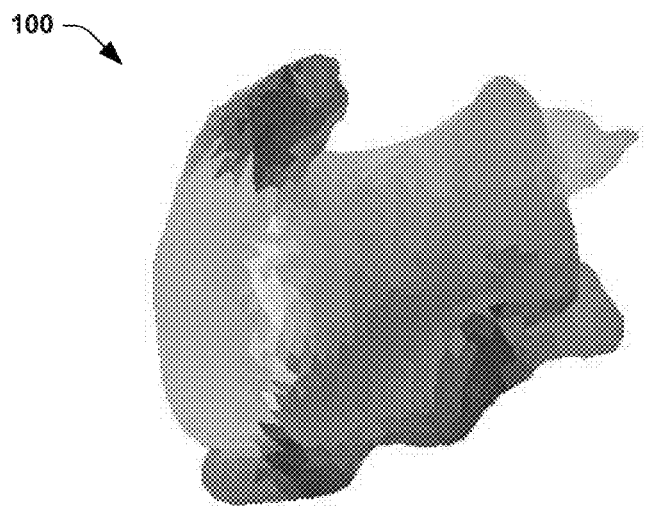
FIG. 5 depicts an example of a physiological map in which phase is mapped to hue according to a color model.
Figure 6:
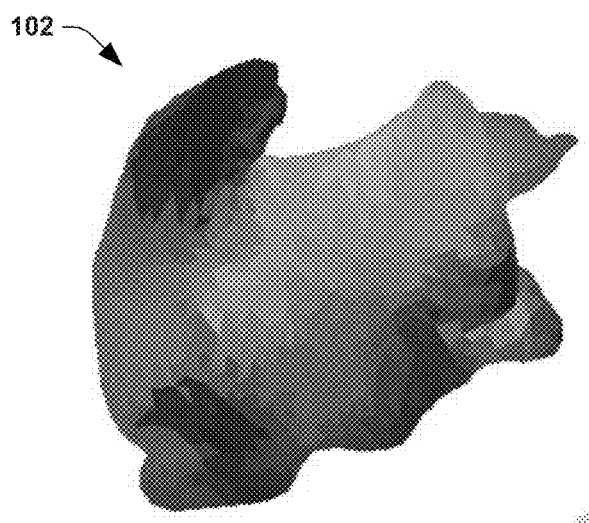
FIG. 6 depicts an example of a physiological map in which phase is mapped to hue and magnitude is mapped to value according to another color model.
Figure 7:
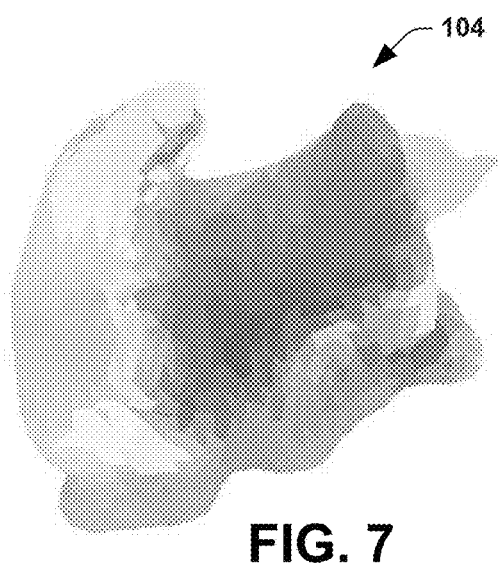
FIG. 7 depicts an example of a physiological map in which phase is mapped to hue and magnitude is mapped to saturation according to an HSV color model.

FIGS. 5, 6 and 7 are examples of cardiac maps 100, 102 and 104 that can be generated by encoding parameters to a geometric surface of the heart according to a selected color model. Each of the examples of FIGS. 5, 6 and 7, utilize an HSV color model to encode phase and magnitude information differently on the surface.

FIG. 5 demonstrates an example of the cardiac map 100 in which phase data is mapped and encoded to hue only and the saturation and value color components are set equal to a fixed value (e.g., s=v=1). FIG. 6 demonstrates an example map 102 in which the phase information is mapped to the hue color component, the saturation color component is set to a fixed value and a normalized magnitude is encoded by the value color component of the HSV color model. In FIG. 7, the map 104 is generated by encoding the phase information as hue and encoding normalized magnitude to the saturation color component. In FIG. 7, the value color component is set to a fixed value.

A comparison of the plots of FIGS. 5, 6 and 7 demonstrates that information can be ascertained upon viewing FIGS. 6 and 7 that is not apparent from the single parameter phase map of FIG. 5. For example, FIGS. 6 and 7 demonstrates that signals at or near the right atrial appendage (RAA) (e.g., corresponding to the upper left corner of each plot) are low magnitude. This is demonstrated by FIG. 6 as a darker region of less value of brightness and in FIG. 7 by faded color (e.g., corresponding to less saturation). Additionally, regions around the left atrial appendage (LAA) have high amplitude signals as demonstrated in FIGS. 6 and 7. The additional information about the amplitude thus can provide an indication of confidence associated with the information presented in the phase only map of FIG. 5. This confidence further can be computed based upon the values encoded in each of the respective maps for the amplitude data. Other indications and parameters associated with cardiac electrical activity can be encoded in a similar manner to provide confidence and understanding of the underlying conditions.

Figure 8:
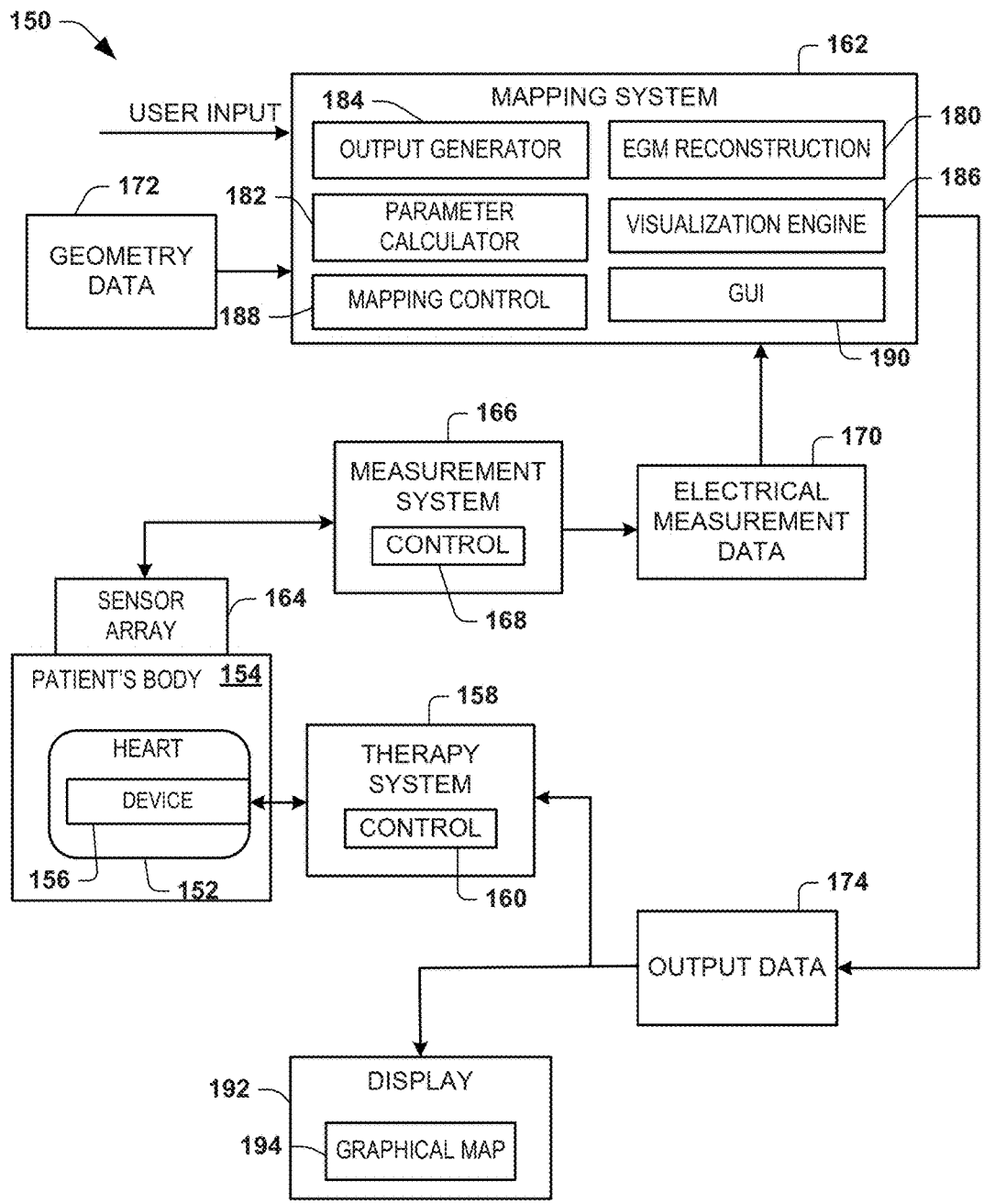
FIG. 8 depicts an example of a system that can generate a multi-parameter map.

FIG. 8 depicts an example of a system 150 that can be utilized for performing diagnostics and/or treatment of a patient. In some examples, the system 150 can be configured to generate multi-parameter physiological maps for the heart 152 in real time as part of a diagnostic or treatment procedure, such as to help a physician determine parameters for delivering a therapy to the patient (e.g., delivery location, amount and type of therapy). For example, a catheter, such as a pacing catheter, having one or more therapy delivery devices 156 affixed thereto can be inserted into the body 154 as to contact the patient's heart 152, endocardially or epicardially. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

The therapy system 158 can be located external to the patient's body 154 and be configured to control therapy that is being delivered by the device 156. For instance, the therapy system 158 includes control circuitry 160 that can communicate (e.g., supply) electrical signals via a conductive link electrically connected between the device (e.g., electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic controls). One or more sensors (not shown) can also communicate sensor information back to the therapy system 158. The position of the device 156 relative to the heart 152 can be determined and tracked intraoperatively via an imaging modality (e.g., fluoroscopy, xray), a mapping system 162, direct vision or the like. The location of the device 156 and the therapy parameters thus can be combined to provide corresponding therapy parameter data.

Before, during and/or after providing a therapy via the therapy system 158, another system or subsystem can be utilized to acquire electrophysiology information for the patient. In the example of FIG. 8, a sensor array 164 includes one or more electrodes that can be utilized for recording patient activity. The sensor array can include electrodes configured to measure the electrical activity form the patient non-invasively, invasively or a combination thereof.

As one example, the sensor array 164 can correspond to a high-density arrangement of body surface sensors (e.g., greater than 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements of sensing electrodes can be used as the sensor array 164. The array can be a reduced set of electrodes, which that does not cover the patient's entire torso and is designed for measuring electrical activity for a particular purpose (e.g., an array of electrodes specially designed for analyzing AF and/or VF) and/or monitoring a predetermined spatial region (e.g., zone) of the heart.

One or more sensors may also be located on the device 156 that is inserted into the patient's body. Such electrode can be utilized in conjunction with the sensor array 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensors, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog and/or digital information.

The control 168 can also be configured to control the data acquisition process for measuring electrical activity and providing the measurement data 170. The measurement data 170 can be acquired concurrently with the delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective data 170 and therapy parameters to facilitate the evaluation and analysis thereof.

The mapping system 162 is programmed to combine the measurement data 170 corresponding to electrical activity of the heart 152 with geometry data 172 by applying appropriate processing and computations to provide corresponding output data 174. The output data 174 can represent or characterize multiple parameters across the geometric surface (e.g., a cardiac envelope of the heart 152).

Since the measurement system 166 can measure electrical activity of a predetermined region or the entire heart concurrently (e.g., where the sensor array 164 covers the entire thorax of the patient's body 154, the resulting output data thus can also represent concurrent data for the predetermined region or the entire heart in a temporally and spatially consistent manner. The time interval for which the output data/maps are computed can be selected based on user input. Additionally or alternatively, the selected intervals can be synchronized with the application of therapy by the therapy system 158.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a geometric surface of the heart, and can include static (three-dimensional at a given instant in time) and/or be dynamic (e.g., four-dimensional map that varies over time). Examples of inverse algorithms that can be utilized in the system 10 are disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more). In other examples, the mapping system 162 can compute electrical activity over a region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed model or a combination thereof (e.g., a model that is modified based on patient anatomy).

As an example, the geometry data 172 may be in the form of graphical representation of the patient's torso, such as based on image data acquired for the patient. Image processing, including extraction and segmentation of anatomical features, can be performed on a digital image set acquired for the patient. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer.

Alternatively, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the geometry data 172 can be acquired using nearly any imaging modality based on which a corresponding representation can be constructed, such as described herein. Such imaging may be performed concurrently with recording the electrical activity that is utilized to generate the patient measurement data 170 or the imaging can be performed separately (e.g., before the measurement data has been acquired).

Following (or concurrently with) determining electrical potential data (e.g., electrogram data computed from non-invasively and/or invasively acquired measurements) across the geometric surface of the heart, the electrogram data can further undergo signal processing to compute one or more cardiac maps. The mapping system 162 can include a parameter calculator 182 that is programmed to compute two or more parameters characterizing cardiac electrical activity for each of a plurality of points in geometric surface of the heart. For example, the parameter calculator 182 can be programmed to compute any of the physiological data disclosed with respect to FIG. 4 (e.g., data 62). As an example, the parameter calculator can compute phase and electrogram magnitude across a given geometric surface of patient tissue (e.g., cardiac tissue or other tissue, such as the brain or other muscles) for one or more time intervals. The magnitude for the plurality of points can be determined as a relative magnitude among the points over the same interval used to compute the phase data.

The output data 174 can be converted to a graphical representation for display by a visualization engine 186. Parameters associated with the visualization, such as including selecting a time interval, a type of information that is to be presented in the visualization and the like can be selected in response to a user input via a corresponding visualization GUI 190. The mapping system 162 thus can generate corresponding output data 174 that can in turn be rendered by the visualization engine 186 as a corresponding graphical output in a display 192, such as including an electrocardiographic map 194 in which multiple parameters are each encoded by different color components of a color model.

In some examples, the control 160 of the therapy system can utilize the output data 174 to control one or more therapy parameters. As an example, the control 160 can control delivery of ablation therapy to a site of the heart (e.g., epicardial or endocardial wall) based on the cardiac information determined from the output data 174 used to generate one or more graphical maps. Other types of therapy can also be controlled based on the output data. The control that is implemented can be fully automated control, semi-automated control (partially automated and responsive to a user input) or manual control based on the output data 174.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware, such as shown and described with respect to the computer system of FIG. 9. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 9:
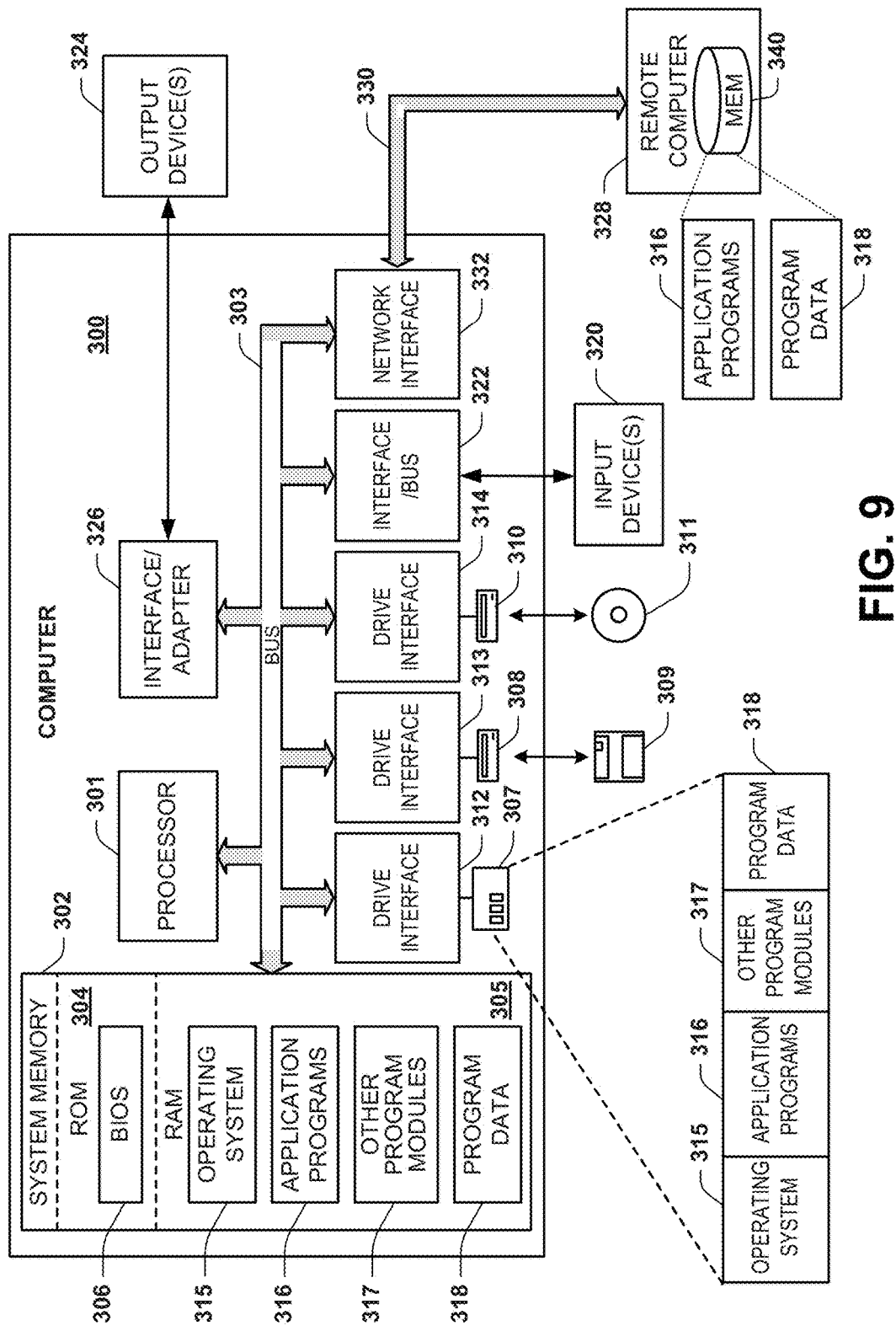
FIG. 9 depicts an example computing environment.

In this regard, FIG. 9 illustrates one example of a computer system 300 that can be employed to execute one or more embodiments, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, smart phone and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the systems and method disclosed herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods (e.g., calculator 12 or 60) programmed to process signals and compute a parameter data. The application programs and program data can also include functions and methods (e.g., map generator 26) programmed to generate one or more multi-parameter maps as well as other electrocardiographic map as disclosed herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims.

Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
   a plurality of sensors configured to measure electrophysiological signals from cardiac tissue associated with a patient;
   an ablation catheter configured to deliver an ablative therapy by applying one or more of heating, cooling and high-frequency; and
   a computing device coupled to the plurality of sensors, the computing device comprising:
      memory storing machine readable instructions and configured to store electroanatomic data; and
      at least one processor configured to access the memory and execute the machine readable instructions,
      wherein the machine readable instructions are further configured to perform, when executed, a method comprising:
         measuring the electrophysiological signals;
         storing the electroanatomic data that corresponds to the electrophysiological signals measured by the plurality of sensors;
         computing phase data for each of a plurality of points of a geometric surface corresponding to the cardiac tissue based on the electroanatomic data for at least one-time interval;
         encoding the phase data to a first color component representing a dimension of a multi-dimensional color model, wherein the multi-dimensional real time model comprises at least two dimensions;
         computing magnitude data for each of the plurality of points of the geometric surface corresponding to the cardiac tissue based on the electroanatomic data for at least one-time interval;
         encoding the magnitude data to a second color component representing another dimension of the multi-dimensional color model; and
         generating the output data corresponding to a multi-parameter graphical map for the geometric surface corresponding to the cardiac tissue of the patient by mapping the phase data to the first color component and the magnitude data to the second color component;
         displaying the multi-parameter graphical map for the geometric surface corresponding to the cardiac tissue of the patient;
         configuring one or more control parameters for delivering the ablative therapy to the cardiac tissue based on the multi-parameter graphical map;
         delivering the ablative therapy to the cardiac tissue according to the one or more control parameters; and
         reconfiguring the one or more control parameters intraoperatively during delivery of the ablative therapy based on one or more changes to the output data reflected in the multi-parameter graphical map.

2. The system of claim 1, the method further comprising normalizing the magnitude data or the phase data to a predetermined scale.

3. The system of claim 2, the method further comprising adjusting a property of the normalizing in response to a user input.

4. The system of claim 1, wherein the multi-parameter graphical map is a first graphical map, the method further comprising generating a second graphical map concurrently with the first graphical map, the second graphical map including only one of the phase data or the magnitude data.

5. The system of claim 1, further comprising control circuitry connected to the ablation catheter, the control circuitry configured to control delivery of the ablative therapy to the cardiac tissue based on the one or more control parameters.

6. The system of claim 5, further comprising one or more sensors located on the ablation catheter to communicate sensor information back to the control circuitry to which the ablation catheter is connected.

7. The system of claim 5, wherein the control system is further configured to provide the one or more control parameters based on a position of the ablation catheter relative to the cardiac tissue.

* * * * *